United States Patent [19]

Ahrens et al.

[11] Patent Number: 5,108,434
[45] Date of Patent: Apr. 28, 1992

[54] LONGITUDINALLY GROOVED SHAFT PROSTHESIS

[75] Inventors: Uwe Ahrens; Curt Kranz; Olaf Neubert; Paul Götsche; Wiebke Ploetz, all of Berlin, Fed. Rep. of Germany

[73] Assignee: Mecron medizinische Produkte GmbH, Berlin, Fed. Rep. of Germany

[21] Appl. No.: 423,150

[22] Filed: Oct. 19, 1989

[30] Foreign Application Priority Data

Oct. 19, 1988 [DE] Fed. Rep. of Germany ....... 3836040

[51] Int. Cl.⁵ .............................................. A61F 2/30
[52] U.S. Cl. ......................................... 623/16; 623/18; 623/66
[58] Field of Search ..................... 623/16, 18, 19, 20, 623/22, 23, 66, 901

[56] References Cited

U.S. PATENT DOCUMENTS 4,623,349  11/1986  Lord ................................... 623/18

Primary Examiner—David J. Isabella
Attorney, Agent, or Firm—Spencer & Frank

[57] ABSTRACT

A shaft prosthesis has an outer surface provided with grooves which extend generally along the length of the prosthesis and which have side walls forming an essentially wedge-shaped cross section terminating at a bottom edge line oriented toward a central longitudinal axis of the prosthesis. Each groove may be divided longitudinally by an imaginary plane; these planes intersect in the central longitudinal axis. The number of grooves in any imaginary angular sector having a vertex line on the center axis increases with increasing distance of the outer surface from the center axis. The grooves extend in close proximity to one another and the grooves extend, while forming branches, over enlarging surface regions which form part of the outer prosthesis surface and which cannot be developed on a plane.

5 Claims, 3 Drawing Sheets

LONGITUDINALLY GROOVED SHAFT PROSTHESIS

BACKGROUND OF THE INVENTION

The present invention relates to a shaft prosthesis which has another surface provided with grooves which extend generally along the length of the prosthesis and which have side walls forming an essentially wedge-shaped cross section terminating at a tip oriented toward a central longitudinal axis of the prosthesis. Each groove defines a plane; these planes intersect in the central longitudinal axis. The number of grooves in an angular region having a vertex on the center axis increases with increasing distance of the outer surface from the center axis.

Shaft prosthesis are known which have grooves extending in the longitudinal direction of the shaft. Similarly to the shaft prosthesis disclosed in European Patent No. 0.145,939, the grooves extend at equal distances from one another on the surface. During the appropriate manufacturing process, the milling cutter or cutters are guided in corresponding tracks which extend at equal distances on the thus produced prosthesis surface whose final outline has already been finish worked.

The drawback is here that with this method it is possible only to create shapes which can be developed into a plane. Moreover, the grooved shaft must have been prefabricated in its basic exterior shape before the grooves are cut.

SUMMARY OF THE INVENTION

It is an object of the present invention to make it possible, to mill grooves on any desired shape of three-dimensional surface.

This object and others to become apparent as the specification progresses, are accomplished by the invention, according to which, briefly stated, the grooves extend in close proximity to one another and the grooves extend, while forming branches, over enlarging surface regions which form part of the outer prosthesis surface and which cannot be developed on a plane.

The invention is based on the realization that grooves, which extend in the longitudinal direction of the shaft, provide good rotational stability and permit removal of the shaft without problems, can also be employed on shafts which widen in space in any desired way or have otherwise irregular shapes. The particular advantage is that the shaft will be able to "seat itself" after implantation by dropping down so that a good seat is ensured.

The number of cutting paths to be traversed during manufacture preferably increases in uniform steps in that at predetermined gradations in the radius, a further path is inserted in the middle between two adjacent paths.

It is particularly favorable that the method according to the invention also permits manufacture by milling from a blank in one process step.

The method according to the invention is particularly suitable for the fully automatic production of shaft prostheses according to individual data obtained from the patient.

In particular, an essentially conical or otherwise tapered milling cutter is provided which is guided on a path in which the pointed end of the cutter is oriented toward a center axis and the cutter travels on individual radial paths which are determined tangentially by the center axis. The number of paths decreases toward the center axis and work progresses in such a manner that the cutter moves along these radial paths and is guided from the outside in to the surface of the prosthesis in its final state. During the removal of individual layers, the cutter follows, in the respective last removal process, the surface of the prosthesis in its finished state. Seen in an axial cross-sectional view, the paths are spaced by at most the distance of one milling cutter working track.

The tip angle of the conical cutter is preferably essentially 30°. During processing, the cutting depth preferably lies in a range from 0.3 to 0.5 mm, if surfaces are involved which are not subjected to any further machining work. To expedite the process and in cases in which the prosthesis components require subsequent working, the cutting depth in a preliminary working stage may initially also be about 1 mm.

A shaft prosthesis produced according to the above-mentioned method is thus particularly distinguished by the fact that the grooves extend in close proximity to one another and that they extend, while forming branches, also over widening surface regions and particularly over surface regions that cannot be developed into a plane.

Advantageous features of the invention are defined in the dependent claims and will be described in greater detail below together with a description of the preferred embodiment of the invention and reference to the drawing figures.

DETAILED DESCRIPTION OF THE PREFERRED EMBODIMENT

Figure 1:
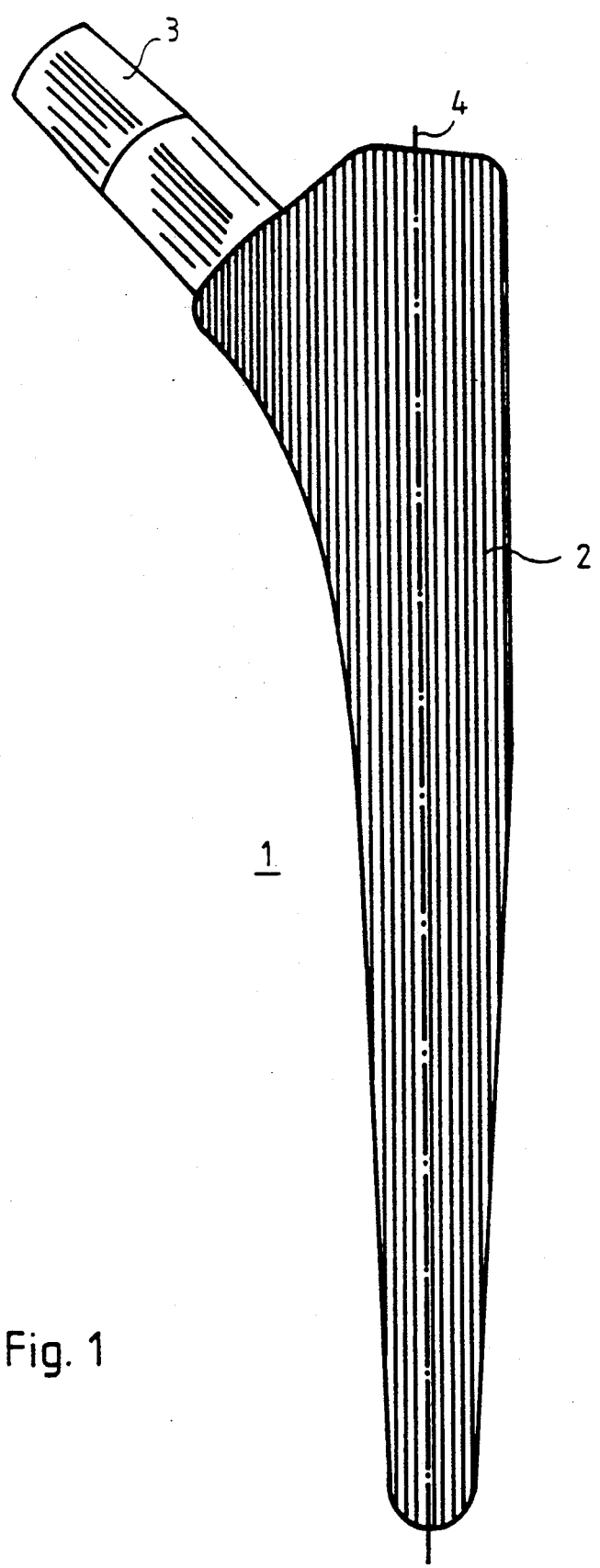
FIG. 1 is a side view of one embodiment of a shaft prosthesis manufactured according to the method of the invention.

In the titanium femur shaft prosthesis 1 shown in FIG. 1 produced according to the method of the invention, a shaft 2 is provided at its proximal end with a cone 3 to accommodate the joint ball. The shaft is provided with grooves 7 which are disposed in close proximity to one another and can be individually geometrically projected—each from a different direction—onto axis 4 (shown in dash-dot lines). Each groove 7 has a bottom edge line 8.

The number of grooves increases with increasing distance from axis 4, with the number of grooves multiplying in the direction of widening in regions whose surface extends at an angle to axis 4. The grooves may here extend, while forming branches, over surface regions which cannot be developed onto a plane; that is, when the surface regions are developed (that is, rolled out) onto an imaginary plane, the surface regions which are protrusions or depressions would not lie in the plane. Rather, such surface regions would lie above or below such plane. Such branches exist particularly in the shaft region which extends in an arc toward cone 3 and are shown individually in the developed enlarged detail view of FIG. 2 to be described below.

Figure 2:
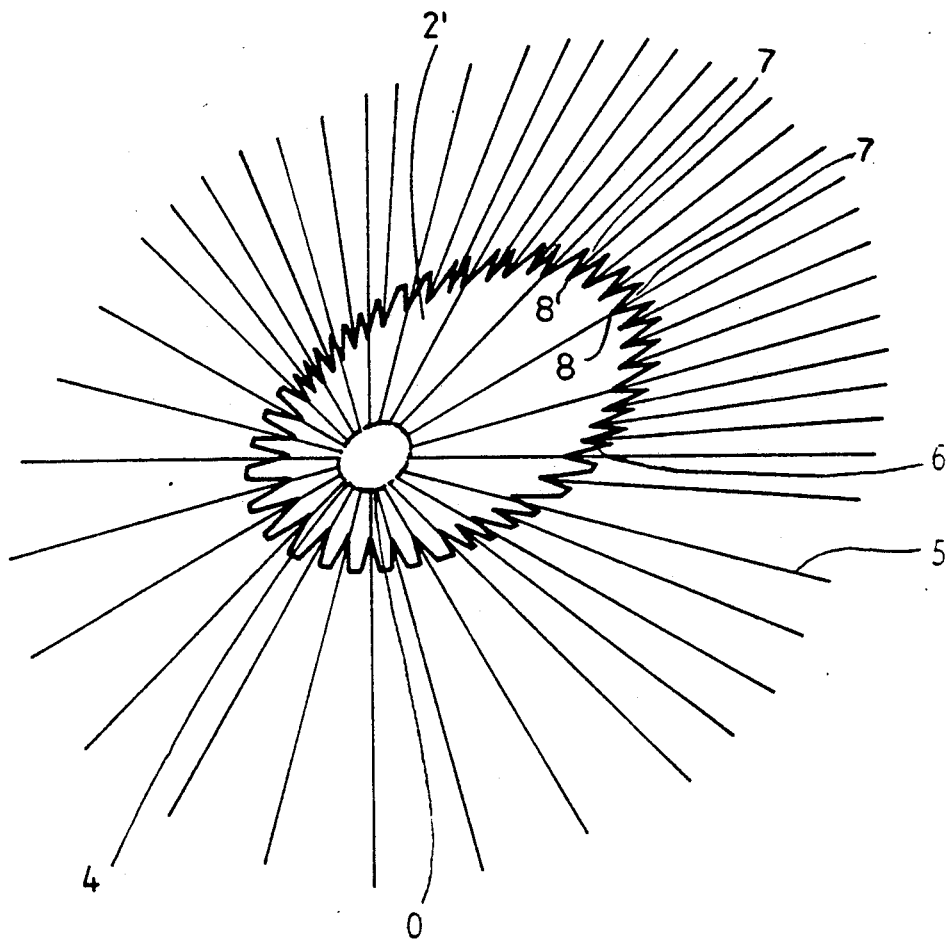
FIG. 2 is a sectional view of a shaft prosthesis in a schematic representation to illustrate the method.

In the illustration of FIG. 2, the sectional view of a different shaft 2' indicates that the grooves in the surface have an essentially wedge-shaped cross section and extend in planes which intersect in a common center axis 4. The bottom edge lines 8 of the wedge-shaped grooves are oriented toward this center axis and the number of grooves associated with an imaginary angular sector having its vertex line on the center axis increases with increasing distance of the surface from the center axis so that the grooves extend in close proximity to one another on the shaft surface.

The straight lines arranged in the manner of a compass dial around axis 4 oriented perpendicularly to the plane of the drawing, some of which intersect in the piercing point trace of axis 4, indicate projections of the planes defined by the lines on which the milling cutter is able to move on its path perpendicular to the plane of the drawing. The number of possible paths increases with increasing radial distance from shaft 4, with the number of cutting paths increasing uniformly in steps in such a manner that, at predetermined gradations of the radius, a further line is inserted in the middle between two adjacent lines so that the distance between two cutting paths does not exceed the width of the path. A cutting path 5 shown as an example belongs to a first group of cutting paths which are sufficiently spaced from one another to be continued to an inner circle 0 inscribed in shaft 2' at a minimum radius to be worked—with respect to the center axis 4 of the shaft (FIG. 1) as the center point of circle 0.

With increasing distance from circle 0, the distance between the cutting paths becomes greater so that further cutting paths are inserted to retain a uniform groove density on the surface of the prosthesis. Path 6 in FIG. 2 is drawn as an example of such a cutting path in a group of identical cutting paths.

Figure 2A:
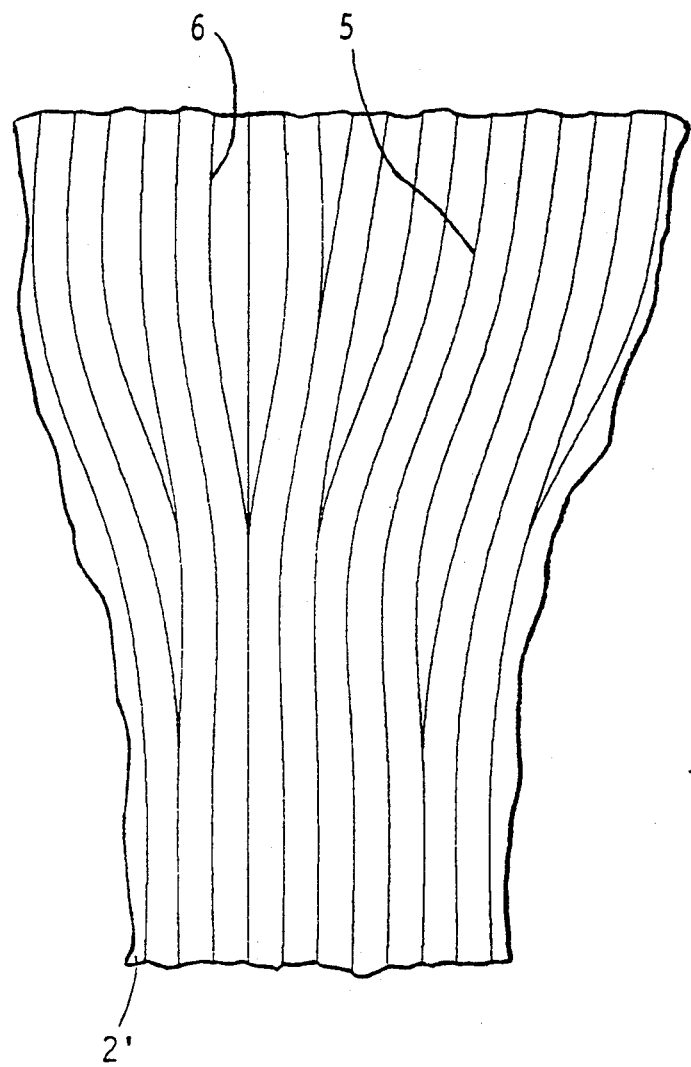
FIG. 2a is a developed side view of a detail of FIG. 2.

FIG. 2a is an enlarged sectional view as a development of shaft surface 2'. While the axis (not shown) of the shaft extends parallel to the plane of the drawing, the outer surface which is illustrated as a top view— seen in the direction from bottom to top—has an increasing curvature toward the observer. The number of cutting paths (for example 5) which were already present in the lower section is increased by additionally inserted grooves (for example 6) which branch off from the original grooves.

In the method of producing the shaft prosthesis, the cutting path for the grooves thus extend in planes which intersect in a common center axis. The tips of the cutting paths whose cross section has a wedge shape are oriented toward this center axis and the number of cutting paths falling into an angular region having its vertex on the center axis increases with increasing distance of the surface from the center axis so that the cutting paths extend in close proximity to one another. The cutting is effected by means of a wedge shaped milling cutter which cuts into a prosthesis blank that does not yet have the outlines of the finished prosthesis (without grooves). Thus what occurs is a complete surface removal process. The number of cutting paths preferably increases uniformly in steps in such a manner that at predetermined gradations of the radius a further path is inserted in the middle between two adjacent paths. The tip angle of the conical milling cutter is essentially 30°.

This method is particularly suitable for the fully automatic production according to data derived from the patient, for example from a computer tomogram.

During working of the shaft shape from the blank, the milling cutter moves in successive passages of the cutting paths on a spiral path from one cutting path to an adjacent cutting path in the direction toward the axis or on concentric circles with increasingly reduced radii or on parts of such paths. If the region of the final outline of the shaft is reached, the path is continued by correspondingly moving back and forth on the free path length between the regions of the remaining shaft outline.

The present invention is not limited in its embodiments to the above-described preferred embodiment. Rather, a number of variations are conceivable which take advantage of the described solution even for basically different configurations. This also includes, in particular, the case where the axis does not extend in a straight line but is slightly bent or even twisted, with the shape of this axis preferably being adapted to the path of the shaft when introduced into the bone.

It will be understood that the above description of the present invention is susceptible to various modifications, changes and adaptations, and the same are intended to be comprehended within the meaning and range of equivalents of the appended claims.

What is claimed is:

1. A prosthesis including an elongated shaft terminating in a proximal end and a distal end; said shaft having a center axis and an outer surface provided with grooves having side walls forming an essentially wedge-shaped cross section terminating in a bottom edge line; the grooves extending substantially longitudinally on said outer surface from said proximal end to said distal end in a substantially uniform density; the bottom edge lines being oriented toward the center axis, whereby a separate imaginary plane longitudinally dividing each groove contains both said center axis and a respective said bottom edge line; and the number of grooves in an imaginary angular sector, having a vertex line coinciding with the center axis, increases with increasing distance of the outer surface from the center axis; the improvement wherein the grooves extend in close proximity to one another; and further wherein the proximal end has an enlarged surface region and said grooves extend from the distal end upward toward the enlarged surface region, and in said enlarged surface region at least some of said grooves forming branches to retain a substantially uniform groove density throughout said enlarged surface region.

2. A prosthesis as defined in claim 1, wherein the number of grooves increases linearly with said increasing distance of the outer surface from the center axis.

3. A prosthesis as defined in claim 1, wherein the number of grooves increases uniformly such that at predetermined increments of said increasing distance of the outer surface from the center axis a further groove is provided on said surface between two adjacent grooves.

4. A prosthesis as defined in claim 1, wherein the side walls of each groove converge at an angle which is essentially 30°.

5. A prosthesis as defined in claim 1, wherein each said groove has a depth between 0.3 and 0.6 mm.

* * * * *